United States Patent [19]

Kawai et al.

[11] Patent Number: 4,540,835
[45] Date of Patent: Sep. 10, 1985

[54] PREPARATION OF 2-TRIFLUOROMETHYLPROPANOL BY VAPOR PHASE HYDROGENATION OF 2-TRIFLUOROMETHYLPROPANAL

[75] Inventors: Toshikazu Kawai, Kamifukuoka; Akira Negishi, Sayama, both of Japan; Iwao Ojima, East Setauket, N.Y.; Takamasa Fuchikami, Sagamihara, Japan

[73] Assignees: Central Glass Company Limited, Ube City; Sagami Chemical Research Center, Tokyo, both of Japan

[21] Appl. No.: 611,081

[22] Filed: May 17, 1984

Related U.S. Application Data

[63] Continuation-in-part of Ser. No. 441,766, Nov. 15, 1982, abandoned.

[30] Foreign Application Priority Data

Nov. 18, 1981 [JP] Japan ................................ 56-183718

[51] Int. Cl.³ ...................... C07C 31/38; C07C 29/132
[52] U.S. Cl. .................................... 568/842; 502/184; 502/185; 549/367
[58] Field of Search ......................................... 568/842

[56] References Cited

U.S. PATENT DOCUMENTS

| | | | |
|---|---|---|---|
| 2,824,897 | 2/1958 | Wujciak et al. | 568/842 |
| 2,982,789 | 5/1961 | Smith et al. | 568/842 |
| 3,356,747 | 12/1967 | Annello et al. | 568/842 |
| 3,440,285 | 4/1969 | Lichstein et al. | 568/842 |
| 3,468,964 | 9/1969 | Swamer | 568/842 |
| 4,467,124 | 8/1984 | Kawai et al. | 568/842 |

FOREIGN PATENT DOCUMENTS

| | | | |
|---|---|---|---|
| 621654 | 4/1949 | United Kingdom | 568/842 |
| 997810 | 7/1965 | United Kingdom | 568/842 |
| 2073181 | 10/1981 | United Kingdom | 568/842 |
| 2087383 | 5/1982 | United Kingdom | 568/842 |

*Primary Examiner*—J. E. Evans
*Attorney, Agent, or Firm*—Fleit, Jacobson, Cohn & Price

[57] ABSTRACT

A process of preparing 2-trifluoromethylpropanol by vapor phase contact reaction between 2-trifluoromethylpropanal trimer and hydrogen in the presence of a catalyst of which the principal component is reduced nickel. The hydrogenation reaction can easily be completed at about 30°–150° C. and at the atmospheric pressure. The starting material is hydrogenated nearly theoretically and with very high selectivity factor for 2-trifluoromethylpropanol.

8 Claims, No Drawings

PREPARATION OF 2-TRIFLUOROMETHYLPROPANOL BY VAPOR PHASE HYDROGENATION OF 2-TRIFLUOROMETHYLPROPANAL

This application is a continuation-in-part of application Ser. No. 441,766, filed Nov. 15, 1982, now abandoned.

BACKGROUND OF THE INVENTION

This invention relates to a process of preparing 2-trifluoromethylpropanol by vapor phase catalytic hydrogenation of the trimer of 2-trifluoromethylpropanal.

Wide uses have been found for 2-trifluoromethylpropanol as industrial material. For example, this compound is useful for esterification of various compounds. Furthermore, by using 2-trifluoromethylpropyl halides it is easy to prepare 2-trifluoromethyl derivatives of various compounds for the purpose of using the derivatives as important raw materials or precursors of some medicines, agricultural chemicals and fluorine-containing polymers.

It was once proposed to prepare 2-trifluoromethylpropanol by liquid phase reduction of methyl 2-trifluoromethylpropionate using lithium aluminum hydride as reducing agent. However, this method has not been put into industrial practice because it is necessary to use the reducing agent in an equimolar proportion to the starting material and, consequently, long and troublesome procedures are needed for isolation of the reaction product.

In general it is known that an aliphatic alcohol can be obtained by liquid phase reduction of a corresponding aliphatic aldehyde or ketone using a metal hydride as reducing agent, but industrially this knowledge has not been utilized either because of the need of using the metal hydride in an equimolar proportion to the starting material. It is also possible to obtain an aliphatic alcohol by hydrogenation of an aliphatic aldehyde or ketone using a metal catalytic such as platinum or palladium. However, it is difficult to apply this method to fluorinated aldehydes or ketones to obtain fluorinated alcohols, and in the cases of industrially favorable vapor phase catalytic hydrogenation very often it is utterly impossible to obtain the intended fluorinated alcohols by reason of significant side reactions and/or decomposition of once formed fluorinated alcohols. For example, U.S. Pat. No. 3,468,964 contains a description that neither 1,1,1,3,3,3-hexafluoropropane-2-ol nor 2,2,2-trifluoroethanol can be obtained by vapor phase contact reaction of hexafluoroacetone or trifluoroacetoaldehyde with hydrogen in the presence of platinum catalyst.

When it is intended to prepare 2-trifluoromethylpropanol by hydrogenation of 2-trifluoromethylpropanal, particularly great difficulties are present because the latter compound is quite liable to undergo association so that not only the monomer having the aldehyde structure of Formula (I) but also an associated polymer, which is usually a trimer having the cyclic ether structure of Formula (II), must be converted to 2-trifluoromethylpropanol.

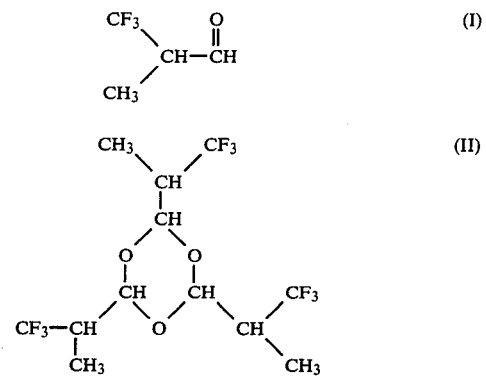

SUMMARY OF THE INVENTION

It is an object of the present invention to provide a novel process of preparing 2-trifluoromethylpropanol by vapor phase catalytic hydrogenation of 2-trifluoromethylpropanal in the form of a trimer, which process realizes very high rate conversion of 2-trifluoromethylpropanal trimer with very high selectivity factor for 2-trifluoromethylpropanol.

According to the invention, 2-trifluoromethylpropanol is prepared by vapor phase contact reaction of 2-trifluoromethylpropanal trimer with hydrogen in the presence of a catalyst which comprises reduced nickel as a principal component thereof.

The catalyst is not required to be reduced nickel alone. That is, reduced nickel may be mixed with or carried on various support or carrier materials used in conventional catalysts for vapor phase contact reactions as will later be described, and the catalyst may be prepared in various forms such as granules or pellets. Furthermore, the catalyst may optionally contain a relatively small amount of at least one base metal other than nickel, such as copper and/or chromium, as an auxiliary catalytic component.

The vapor phase catalytic hydrogenation reaction according to the invention is carried out at relatively low temperatures such as about 30°–150° C. and smoothly proceeds even at the atmospheric pressure.

It is an important advantage of the process of the invention that the trimer of 2-trifluoromethylpropanal formed by spontaneous association thereof can easily and surely be converted to 2-trifluoromethylpropanol. That is, our process can be started without the need of precedingly dissociating the associated material to 2-trifluoromethylpropanal monomer by a troublesome procedure, e.g. by distillation with the addition of a Lewis acid such as boron trifluoride or aluminum chloride. Though less of importance from a practical point of view, this process is applicable also to the conversion of the monomer of 2-trifluoromethylpropanal, or a polymolecular compound other than trimer formed by spontaneous association of the monomer, to 2-trifluoromethylpropanol.

The hydrogenation reaction in this process can be represented by the following equation.

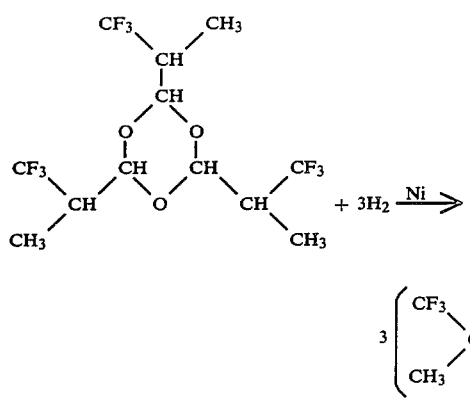

It is our discovery that this reaction is realized by using reduced nickel as catalyst. Also we have confirmed that other metal catalytics commonly used in vapor phase contact reactions, such as platinum and palladium as typical examples, are utterly ineffective for conversion of 2-trifluoromethylpropanal in the form of either trimer or monomer to 2-trifluoromethylpropanal.

Besides the above described advantage, the present invention has the following advantages and is very suited to industrial application. This process utilizes an inexpensive catalyst, and this process can be performed as a continuous process under mild reaction conditions. The desired compound can be prepared with very high yield and without suffering from decomposition or further hydrogenation of that compound, and accordingly no particular operation is needed for isolation of the product of the hydrogenation reaction.

DESCRIPTION OF THE PREFERRED EMBODIMENTS

The starting material for the process of the invention, 2-trifluoromethylpropanal, can easily be prepared by, for example, reaction of 3,3,3-trifluoro-1-propene with carbon monoxide and hydrogen in the presence of a complex compound of a Group VIII metal. This compound is quite liable to undergo association to form a trimer as mentioned hereinbefore, but there is no need of dissociating the associated starting material in advance of the hydrogenation process.

To realize vapor phase contact reaction of 2-trifluoromethylpropanal trimer with hydrogen to form exclusively 2-trifluoromethylpropanol, the process of the invention always employs a catalyst of which the principal component is reduced nickel. As is well known, so-called reduced nickel is a metallic nickel obtained, for example, by reduction of a suitable nickel compound such as nickel carbonate, nickel oxide or nickel hydroxide in a hydrogen gas atmosphere or by thermal decomposition reduction of nickel salt of an organic acid such as nickel formate, nickel oxalate or nickel acetate in an oxygen-free atmosphere. Of course it is possible to use a catalyst substantially wholly consisting of reduced nickel, but it is also possible and rather convenient in practice, to use a catalyst in which reduced nickel is mixed with or carried by noncatalytic or somewhat catalytic substances that serve as support or carrier materials. The latter catalyst is usually prepared in the form of granules or pellets. As to the support or carrier materials, graphite, alumina, magnesia, activated carbon, diatomite (kieselguhr) and terra alba can be named as suitable examples. Optionally and rather preferably, the catalyst may contain copper and/or chromium as an auxiliary catalytic component. Also optionally, the catalyst may contain manganese, zirconium, aluminum and/or cobalt for the purpose of promoting the activity of nickel on the intended hydrogenation reaction or suppressing poisoning of the catalyst by the influence of a certain impurity such as sulfur. It is permissible that these base metals optionally added to the catalyst, including copper and chromium, partly exist as respective oxides. It is suitable that the total amount of the optionally added base metal(s) is up to 10% by weight of nickel in the catalyst. Usually it suffices that the reduced nickel in the catalyst amounts to 0.01 to 20% by weight of 2-trifluoromethylpropanal trimer to be hydrogenated.

It is possible to obtain a reduced nickel catalyst from a nickel catalyst in which nickel is in the state of its oxide by a reduction treatment of the nickel catalyst in the reactor for the preparation of 2-trifluoromethylpropanol immediately before starting the hydrogenation process. For example, the reduction treatment is carried out by gradually heating the catalyst up to 150°-200° C. in a hydrogen gas stream and maintaining that temperature until completion of the reaction of nickel oxide with hydrogen to form elemental nickel and water. Even in the case of using a reduced nickel catalyst, it is recommended to perform a similar reduction treatment to thereby preliminarily activate the catalyst since reduced nickel gradually undergoes air oxidation during storage before use.

As to the quantity of hydrogen gas for use in the hydrogenation process, the minimum requirement is to use one mole of hydrogen per one mole of 2-trifluoromethylpropanal (as monomer) to be hydrogenated. There arises no problem by using excess quantity of hydrogen gas for the purpose of using it also as carrier gas for 2-trifluoromethylpropanal.

The vapor phase contact reaction according to the invention is carried out at relatively low temperatures. Of course the reaction temperature must be above a temperature at which the starting material, the trimer of 2-trifluoromethylpropanal, vaporizes but should not be so high as will cause perhydrogenation of 2-trifluoromethylpropanol formed by the reaction. Within these limitations the reaction temperature can arbitrarily be determined, and usually it is suitable to employ a reaction temperature in the range from about 30° C. to about 150° C., and more preferably in the range from 50° to 130° C. The intended reaction smoothly proceeds and can be completed at the atmospheric pressure, but it is optional and raises no problem to carry out the reaction at a somewhat elevated or reduced pressure.

In this hydrogenation process, usually a contact time ranging from a few seconds to several minutes is sufficient to complete the intended reaction. However, even when the contact time is made more longer the desired compound, 2-trifluoromethylpropanol, can be formed almost theoretically without the fear of its perhydrogenation.

Hereinafter the present invention will be illustrated by several examples without the least intention of limiting the invention in any respect.

EXAMPLE 1

To prepare a reduced nickel catalyst, use was made of a nickel oxide catalyst which was in the form of pellets 5 mm in diameter and composed of 57.3–59.8 wt% of NiO, 2.9–4.4 wt% of $Cr_2O_3$, 2.5–3.8 wt% of CuO, 27–29 wt% of diatomite and 4–5 wt% of graphite. In a Pyrex tube having an inner diameter of 13 mm, 25 g of this catalyst was packed and subjected to a reduction and preliminary activation treatment, which was carried out by continuously passing hydrogen gas through the tube at a rate of 300 ml/min while gradually raising the temperature up to 200° C. and maintaining this temperature for about 3 hr until the formation of water terminated. It was confirmed that the treated catalyst had turned into a reduced nickel catalyst consisting of 54.0–56.3 wt% of Ni, 2.5–3.4 wt% of Cr, 2.5–3.4 wt% of Cu, 33.3–33.8 wt% of diatomite and 5.0–5.7 wt% of graphite. Thereafter the catalyst was maintained at 95° C.

Then a mixed gas of vaporized 2-trifluoromethylpropanal trimer (30 g/hr) and hydrogen (14.4 l/hr) was continuously passed through the tube packed with the reduced nickel catalyst to cause hydrogenation of 2-trifluoromethylpropanal trimer by vapor phase contact reaction. The reaction temperature in the reaction tube was maintained at about 95° C.

The length of the packed catalyst column in the reaction tube and the flow rate of the mixed gas were such that the contact time in this hydrogenation reaction was about 7 seconds. In this case the amount of the hydrogen gas in the mixed gas was calculated to be about 2.7 moles per one mole of 2-trifluoromethylpropanal (as monomer). The reaction was continued for 7 hr, while the reaction product was collected by water cooling of the reacted gas. Upon completion of the reaction the product was confirmed to be about 212 g 2-trifluoromethylpropanol of which the purity was 99.0%. In this reaction, the conversion of the supplied 2-trifluoromethylpropanal trimer was 99.8%, and the selectivity factor for 2-trifluoromethylpropanol was 100%.

The thus prepared 2-trifluoromethyl propanol exhibited the following characteristics. Boiling point ($b_{760}$): 110.0° C.

Refractive index ($n_D^{22}$): 1.3422

IR (neat): 3350 $cm^{-1}$ ($\nu_{O-H}$)

$^1H$ NMR ($CCl_4$; TMS): δ 1.17 (doublet, J=7.5 Hz, 3H), 2.32 (multiplet, 1H), 3.74 (singlet, 1H), 3.57 (doublets of doublets, J=11.7 Hz, J=5.9 Hz, 1H), 3.77 (doublets of doublets, J=11.7 Hz, J=5.8 Hz, 1H).

$^{19}F$ NMR ($CCl_4$; $CF_3COOH$): δ −6.17 (doublet, J=8.2 Hz).

COMPARATIVE EXAMPLE 1

A mixed gas of vaporized 2-trifluoromethylpropanal monomer (30 g/hr) and hydrogen (14.4 l/hr) was continuously supplied into a reaction tube packed with the reduced nickel catalyst described in Example 1, maintaining a constant reaction temperature of 90° C. Also in this reaction the contact time was about 7 sec. In this example the conversion of 2-trifluoromethylpropanal monomer was calculated to be 99.0%, and the selectivity factor for 2-trifluoromethylpropanol was 100%.

EXAMPLE 2

To prepare a reduced nickel catalyst, use was made of a nickel oxide catalyst which was in the form of pellets 5 mm in diameter and composed of 62.4–66.6 wt% of NiO, 27–29 wt% of diatomite and 4–5 wt% of graphite. In the same Pyrex tube as the one used in Example 1, 25 g of the nickel oxide catalyst was packed and subjected to a reduction and preliminary activation treatment, which was identical with the treatment in Example 1. It was confirmed that the treated catalyst had turned into a reduced nickel catalyst consisting of 60.5–61.3 wt% of Ni, 33.7–33.8 wt% of diatomite and 5.0–5.8 wt% of graphite. Thereafter the catalyst was maintained at 140° C.

Then a mixed gas of vaporized 2-trifluoromethylpropanal trimer (60 g/hr) and hydrogen (28.8 l/hr) was continuously passed through the reaction tube packed with the reduced nickel catalyst. The hydrogenation reaction proceeded rapidly and smoothly, so that the reaction temperature in the tube soon rose to 145° C., and thereafter this temperature was maintained. In this reaction the contact time was about 3 sec, and the amount of hydrogen in the mixed gas was about 2.7 moles per one mole of 2-trifluoromethylpropanal (as monomer). In this example the conversion of 2-trifluoromethylpropanal trimer was 100%, and the selectivity factor for 2-trifluoromethylpropanol was 92%.

COMPARATIVE EXAMPLE 2

A mixed gas of vaporized 2-trifluoromethylpropanal monomer (10 g/hr) and hydrogen (7.2 l/hr) was continuously supplied to a reaction tube packed with the reduced nickel catalyst described in Example 2, maintaining a constant reaction temperature of 55° C. In this reaction the contact time was about 13 sec. In this example the conversion of 2-trifluoromethylpropanal was 99%, and the selectivity factor for 2-trifluoromethylpropanol was 96%.

REFERENCE

For comparison, 10 g of a palladium catalyst in the form of pellets 3 mm in diameter containing 0.5% of Pd supported on alumina carrier was packed in the same reaction tube as the one used in Example 1, and a mixed gas of vaporized 2-trifluoromethylpropanal trimer (30 g/hr) and hydrogen (14.4 l/hr) was continuously supplied into the reaction tube. In this experiment the reaction temperature was maintained at 90° C., and the contact time was 4 sec. Upon completion of the reaction it was confirmed that not the least quantity of 2-trifluoromethylpropanol had been formed, though the entire quantity of the supplied 2-trifluoromethylpropanal trimer had decomposed.

EXPERIMENT

By way of example, 2-trifluoromethylpropanal was prepared by the following process.

Charged into an autoclave having a capacity of 200 ml were 20.7 mg of chlorocarbonyl-bis-(triphenylphosphine)rhodium ($3.00 \times 10^{-2}$ millimoles), 224 ml of gaseous 3,3,3-trifluoro-1-propene (10.0 millimoles) and 2 ml of toluene which was used as solvent. Then carbon monoxide gas and hydrogen gas were filled into the autoclave such that the partial pressures of carbon monoxide and hydrogen became respectively 40 atm. The thus pressurized reaction system in the autoclave was stirred and heated to and maintained at 110° C. The reaction was completed by continuing the stirring and heating for 16 hr, and 1.20 g of crude 2-trifluoromethylpropanal was obtained by distillation of the reacted mixture, meaning that the yield was 95%.

What is claimed is:

1. A process of preparing 2-trifluoromethylpropanol, comprising the step of allowing a vaporized trimer of 2-trifluoromethylpropanal to contact and react with hydrogen gas in the presence of a catalyst which comprises reduced nickel as a principal component thereof.

2. A process according to claim 1, wherein the vapor phase contact reaction between said trimer and hydrogen gas is carried out at a temperature in the range from about 30° C. to about 150° C.

3. A process according to claim 2, wherein said temperature is in the range from 50° to 130° C.

4. A process according to claim 2, wherein said vapor phase reaction is carried out by continuously passing said trimer and hydrogen gas through a reaction chamber in which is dispoed said catalyst.

5. A process according to claim 4, wherein said reaction is carried out substantially at the atmospheric pressure.

6. A process according to claim 1, wherein said catalyst further comprises at least one base metal selected from the group consisting of copper, chromium, manganese, zirconium, aluminum and cobalt as an auxiliary component, the total amount of said at least one base metal being not larger than 10% by weight of said reduced nickel.

7. A process according to claim 6, wherein said catalyst further comprises at least one supporting material selected from the group consisting of graphite, diatomite, terra alba and activated carbon.

8. A process according to claim 1, wherein said catalyst further comprises at least one supporting material selected from the group consisting of graphite, diatomite, terra alba and activated carbon.

* * * * *